United States Patent [19]
Enhsen et al.

[11] Patent Number: 6,090,190
[45] Date of Patent: Jul. 18, 2000

[54] CLOSURE SYSTEMS FOR CHROMATOGRAPHIC COLUMNS

[75] Inventors: Alfons Enhsen, Büttelborn; Ralf Watkowiak, Eppstein, both of Germany

[73] Assignee: Hoechst Marion Roussel Deutschland GmbH, Frankfurt am Main, Germany

[21] Appl. No.: 09/209,286

[22] Filed: Dec. 11, 1998

[30] Foreign Application Priority Data

Dec. 12, 1997 [DE] Germany .......................... 197 55 244

[51] Int. Cl.$^7$ .............................. B01D 15/08; F16L 37/20
[52] U.S. Cl. ........................ 96/101; 96/106; 210/198.2; 285/364; 285/394; 285/406
[58] Field of Search .................. 96/101–107; 210/198.2; 285/80, 363, 364, 394, 406

[56] References Cited

U.S. PATENT DOCUMENTS

| | | | |
|---|---|---|---|
| 3,250,395 | 5/1966 | Blume | 210/198.2 X |
| 3,346,486 | 10/1967 | Winter et al. | 210/198.2 X |
| 3,474,908 | 10/1969 | Catravas | 210/198.2 |
| 4,289,620 | 9/1981 | Hara | 210/198.2 |
| 4,313,828 | 2/1982 | Brownlee | 210/198.2 |
| 4,451,363 | 5/1984 | Brownlee et al. | 210/198.2 |
| 4,451,364 | 5/1984 | Higgins et al. | 96/104 X |
| 4,737,284 | 4/1988 | Hauke et al. | 96/104 X |
| 4,806,238 | 2/1989 | Sättler et al. | 96/104 X |
| 4,865,728 | 9/1989 | Larsson | 96/106 X |
| 5,462,659 | 10/1995 | Saxena et al. | 96/106 X |
| 5,601,708 | 2/1997 | Leavesley | 96/101 X |

*Primary Examiner*—Robert H. Spitzer
*Attorney, Agent, or Firm*—Finnegan, Henderson, Farabow, Garrett & Dunner, L.L.P.

[57] ABSTRACT

A device for establishing a flange connection, having a bearing which can act on a first flange, a counter-bearing which can act on a second flange, and a connecting lever between the two bearings is described. The invention is distinguished by the fact that the connecting lever is a lever with a drawing element. The drawing element and the lever each have a first and second end. The drawing element's first end engages the bearing and its second end jointedly mounts in between the first and second ends of the lever. The counter-bearing has at least one contact location for the first end of the lever and a recess for the drawing element.

24 Claims, 3 Drawing Sheets

CLOSURE SYSTEMS FOR CHROMATOGRAPHIC COLUMNS

The invention relates to a connection and closure system for chromatographic columns.

In chromatographic systems used thus far, screw and flange connections have been predominantly used for the connection and closure of chromatographic columns.

Screw closures are used, for example, as closures of chromatographic columns made of glass and metal. In these closures, both the column tube and the so-called column head are threaded (internal and external thread, respectively). The two parts are then screwed together along with the associated seal, which is usually on the end of the column tube. Thus, together with the seal lying in between the column tube and head a pressure tight connection is produced.

Flange connections are also used as closures of chromatographic columns made of glass and metal. In these closures, a first ring of metal is pushed over the glass tube, which represents the column, and is arranged behind the flange, which closes off the glass tube. A second ring is pushed in a corresponding way over the closure part, which forms the counter-flange. Both rings are provided with large bores, so that when the flanges (along with the associated seal) are brought into their intended position the rings can be connected by means of screws. The flanges and the seal, which lies in between pressed against one another to produce a pressure tight connection. The first flange thereby forms a bearing and the second flange a counter-bearing for the screw connection.

These known connections have a disadvantage. They can only be established and undone again by spending a comparatively long time. In addition, the threads in the screw-in connections are easily damaged by finely dispersed material filling the columns or by canting. Both result in leakages and pressure losses. To re-establish a fully serviceable connection, the threads both in the column tube and in the column head must be reworked. The flange connections, besides taking a comparably long time to establish and disestablish, have another disadvantage, depending on the column diameter, several screwed unions (usually 4 to 10) have to be adjusted and tightened exactly with the same torque in order to assure that no stresses occur in the union. It is particularly important that no stresses occur in the union when working under high pressure (HPLC).

The invention was designed, therefore, to accomplish the object of providing a flange connection which can be operated more simply, quickly and reliably.

This object is achieved by a device according to the main claim.

The subject of the invention, therefore, is a device for establishing a flange connection, having a bearing which can act on a first flange, a counter-bearing which can act on a second flange, and a means for connecting the two bearings. The means are provided in the form of a lever with a drawing element, the drawing element and lever each having a first and a second end, wherein the drawing element can engage with its first end into the bearing and its second end is jointedly mounted between the first and second ends of the lever.

The counter-bearing has at least one contact location for the first end of the lever and also a recess for the drawing element. Further, the means are designed in such a way that, when the device is operated in the intended manner, the drawing element or each drawing element engages in the bearing and the first end or each first end of the lever or each lever engages in the contact location or each contact location of the counter-bearing. In addition, when the second end or each second end of the lever or each lever moves into an end position, the first end or each first end remaining in the contact location or each contact location, the drawing element or each drawing element fits into the recess or each recess and presses the first and second flanges together to form a pressure tight connection.

Preferred embodiments of the invention emerge from the subclaims. One or more of the embodiments disclosed in the subclaims may also in themselves or in combination represent solutions achieving the underlying object, and the individual features within the categories of claims can also be combined in any way desired.

The drawing element may be a bar made of metal which has a thread at its first end and can be fastened in the bearing by means of nuts. However, an adequately strong spring made of metal may also be used as the drawing element. In a preferred configuration, two drawing elements are connected by means of a common lever comprising two bores by which the second ends of the drawing elements are connected to the common lever.

Suitable materials are the customary metallic materials, preferably rust- and/or acid-resistant steels, as well as plastics, preferably of high strength. The outside diameter of the bearings may be slightly or greatly larger than the inside diameter of the tubes, preferably in the range from 50 to 150 mm.

The device according to the invention has, inter alia, the advantage that a uniform setting of the drawing elements is required only once, so that further closing can be carried out more quickly and without leakages occurring. The device according to the invention is particularly suitable for connecting tubes, whether they are made of glass or metal or plastic, with an inside diameter preferably from the range from 20 to 100 mm, but also larger. A preferred field of application is that of medium pressure chromatography, that is to say connecting or closing chromatographic columns which must withstand an internal pressure from the range from 1 to about 40 bar. Here, inside diameters of up to or even greater than 500 mm can occur on the pilot plant scale, preferably up to 500 mm.

An exemplary configuration of the invention is described in more detail below with reference to FIGS. 1 and 2. Another configuration of the invention is described in detail below with reference to FIG. 3. These are not intended in any way to restrict the invention.

DETAILED DESCRIPTION OF THE DRAWINGS

FIG. 1

Figure 1:
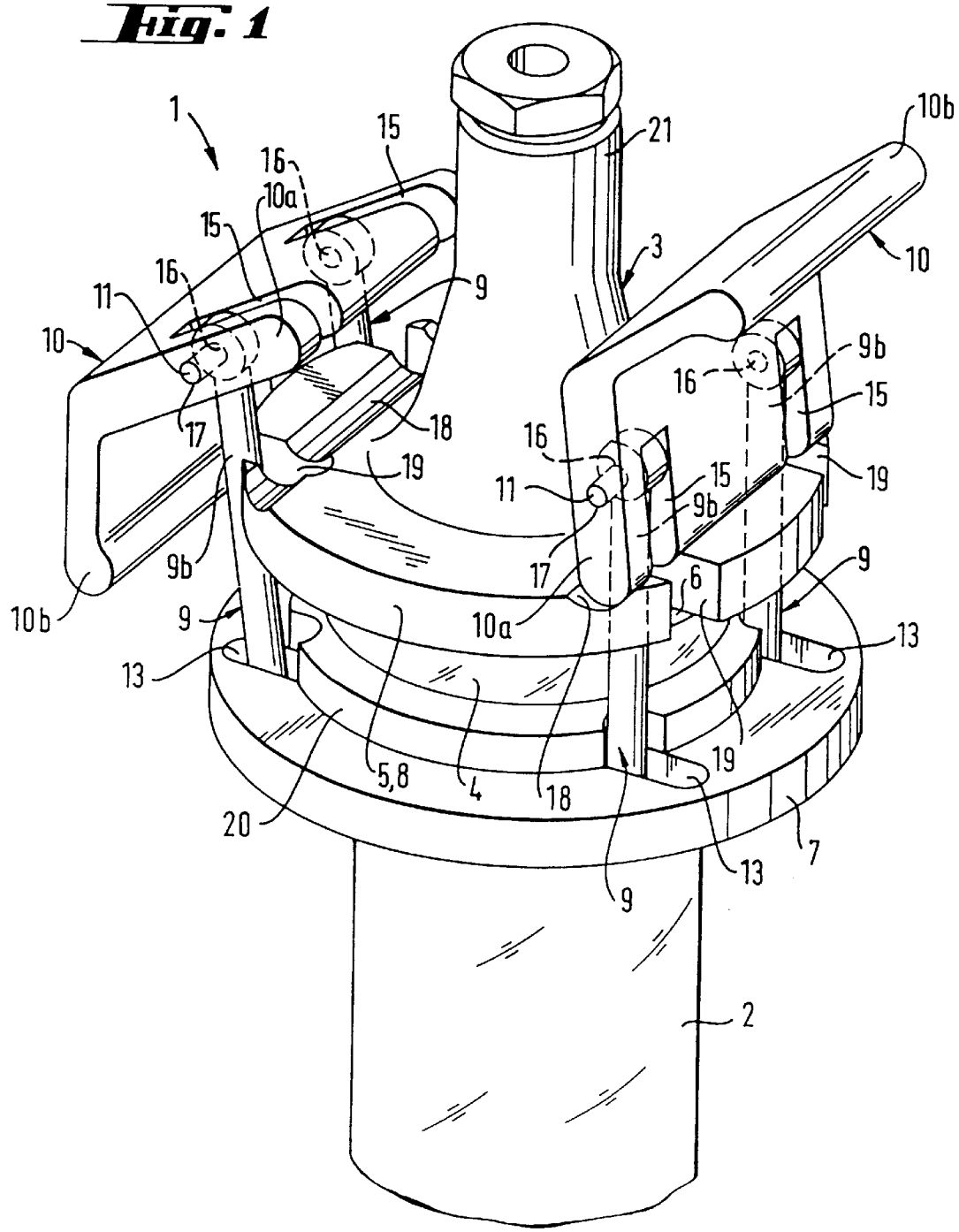
FIG. 1 shows a diagram of a chromatographic column, closed with the aid of a device according to the invention, in a perspective side view.
Figure 2:
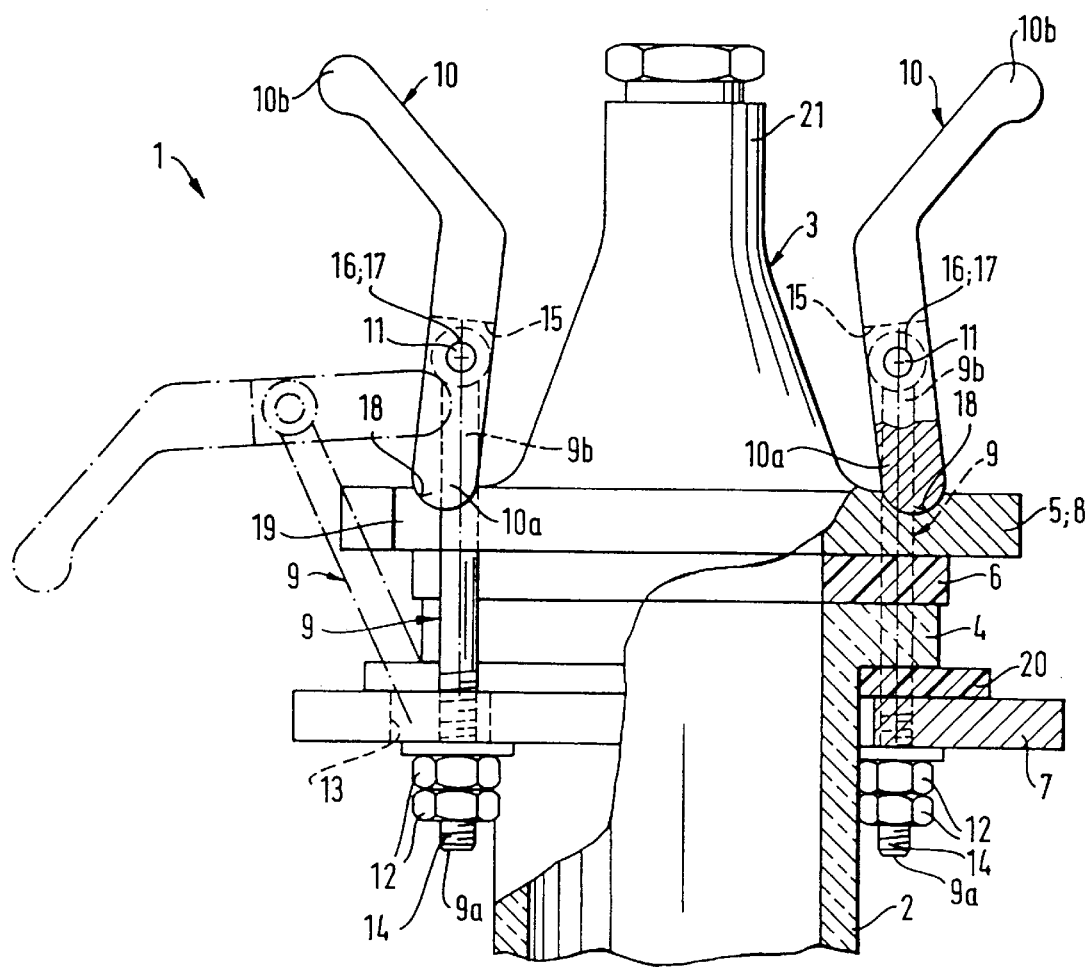
FIG. 2 shows a side view of the closure device and the column from FIG. 1, partially in section.
Figure 3:
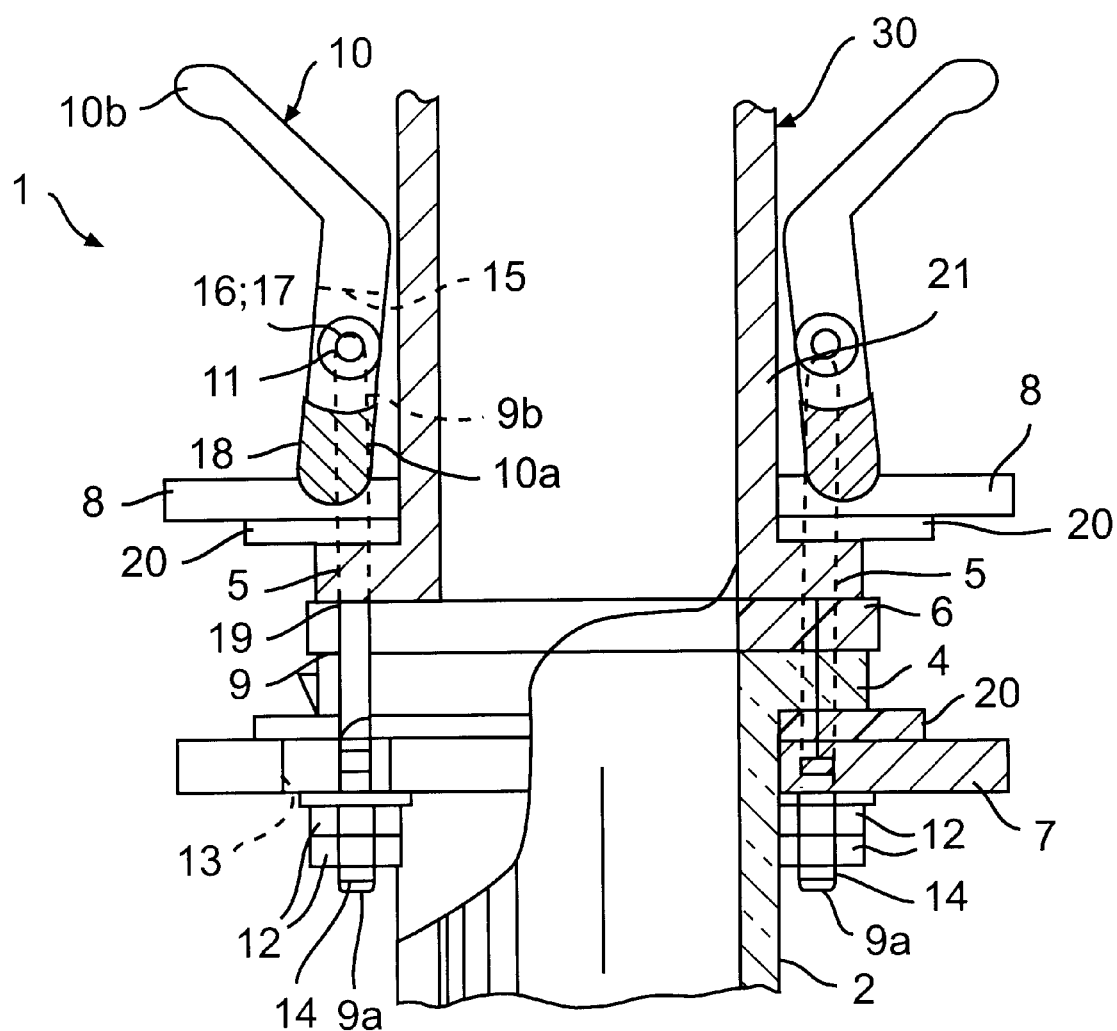
FIG. 3 shows a side view of a closure/connection device and the column, partially in section.

It is shown how a closure device 1 according to the invention is used to close a chromatographic column 2, in the present case a glass tube, by means of a metal cap 3. The glass tube 2 has a first flange 4. The metal cap has the matching second flange 5. Inserted between these two flanges in the closed state is a seal 6. The closure device 1 comprises a first metal ring 7, which is arranged behind the first flange 4 and acts as a bearing. The closure device 1 also comprises a second metal ring 8, which in this example is identical to the second flange 5, which is fitted on a closure piece 21 and acts as a counter-bearing. The closure device 1 also comprises four drawing means, which are designed as bars 9, for connecting the metal rings 7 and 8, two levers 10 each having a first end 10a and a second end 10b, bolts 11, and nuts 12.

FIG. 2

Within the metal ring 7 are four holes 13, corresponding to the number of bars 9. The bars 9 are inserted through these holes 13 by their first end 9a, which has a thread 14, and are fixed by means of the nuts 12. The second end of the bars 9b has bores 16 and is jointedly mounted in recesses 15 of the levers 10 by means of bolts 11, which engage in the bores 16 and corresponding bores 17 in the levers 10. The levers 10 are designed in such a way that they can each receive two bars 9, whereby the two bars 9 can be operated simultaneously. Furthermore, the bars 9 are guided in the recesses 15 when the closure device is operated and extend in these recesses 15 in the end position (closure position). For simpler handling, the levers 10 are of an angled form.

Milled in the second metal ring 8 are two grooves 18, which serve as contact locations for the levers 10. There are also recesses 19 in the corresponding counter-positions with respect to the holes 13. To avoid damage to glass parts, in particular the flange 4, a ring 20 made of flexible material, preferably of plastic, is inserted between the first flange 4, which in this example consists of glass, and the metal ring 7.

FIG. 3

It is shown how a closure device 1 according to the invention is used to connect a chromatographic column 2, in the present case a glass tube, to a corresponding chromatographic column 30. The glass tube 2 has a first flange 4. The corresponding column has a matching second flange 5. Inserted between these two flanges in the closed state is a seal 6. The closure device 1 comprises a first metal ring 7, which is arranged behind the first flange 4 and acts as a bearing. The closure device 1 also comprises the second flange 5 arranged below a spacer ring 20 arranged below a second metal ring 8. The metal ring 8 is fitted on a closure piece 21 and acts as a counter-bearing. The closure device 1 also comprises four drawing means, which are designed as bars 9, for connecting the metal rings 7 and 8, two levers 10, bolts 11, and nuts 12.

Within the metal ring 7 are four holes 13, corresponding to the number of bars 9. The bars 9 are inserted through these holes 13 by their first end 9a, which has a thread 14, and are fixed by means of the nuts 12. The second end of the bars 9b has bores 16 and is jointedly mounted in recesses 15 of the levers 10 by means of bolts 11, which engage in the bores 16 and corresponding bores 17 in the levers 10. The levers 10 are designed in such a way that they can each receive two bars 9, whereby the two bars 9 can be operated simultaneously. Furthermore, the bars 9 are guided in the recesses 15 when the closure device is operated and extend in these recesses 15 in the end position (closure position). For simpler handling, the levers 10 are of an angled form.

Milled in the second metal ring 8 are two grooves 18, which serve as contact locations for the levers 10. There are also recesses 19 in the corresponding counter-positions with respect to the holes 13. To avoid damage to glass parts, in particular the flange 4, a ring 20 made of flexible material, preferably of plastic, is inserted between the first flange 4, which in this example consists of glass, and the metal ring 7.

We claim:

1. A device for establishing a flange connection, having a bearing which can act on a first flange, a counter-bearing which can act on a second flange, and also means for connecting the two bearings, wherein the means are provided in the form of a lever with a drawing element, the drawing element and lever each having a first and second end, wherein the drawing element can engage with its first end into the bearing and its second end is jointedly mounted between the first and second ends of the lever, wherein the counter-bearing has at least one contact location for the first end of the lever and also a recess for the drawing element and wherein the means are designed in such a way that, when the device is operated in the intended manner, the drawing element or each drawing element engages in the bearing and the first end or each first end of the lever or each lever engages in the contact location or each contact location of the counter-bearing, and wherein, when the second end or each second end of the lever or each lever moves into an end position, the first end or each first end remaining in the contact location or each contact location, the drawing element or each drawing element fits into the recess or each recess and presses the first and second flanges together to form a pressure-tight connection.

2. The device as claimed in claim 1, wherein the bearing and the first flange are identical.

3. The device as claimed in claim 2, wherein the counter-bearing and the second flange are identical.

4. The device as claimed in claim 3, wherein the device has four drawing elements, of which two are respectively connected by means of a common lever.

5. The device as claimed in claim 4, wherein the drawing elements are bars.

6. The device as claimed in claim 4, wherein the drawing elements are metal springs.

7. The device as claimed in claim 3, wherein the drawing elements are bars.

8. The device as claimed in claim 3, wherein the drawing elements are metal springs.

9. The device as claimed in claim 2, wherein the device has four drawing elements, of which two are respectively connected by means of a common lever.

10. The device as claimed in claim 9, wherein the drawing elements are bars.

11. The device as claimed in claim 9, wherein the drawing elements are metal springs.

12. The device as claimed in claim 2, wherein the drawing elements are bars.

13. The device as claimed in claim 2, wherein the drawing elements are metal springs.

14. The device as claimed in claim 1, wherein the counter-bearing and the second flange are identical.

15. The device as claimed in claim 14, wherein the device has four drawing elements, of which two are respectively connected by means of a common lever.

16. The device as claimed in claim 15, wherein the drawing elements are bars.

17. The device as claimed in claim 15, wherein the drawing elements are metal springs.

18. The device as claimed in claim 14, wherein the drawing elements are bars.

19. The device as claimed in claim 14, wherein the drawing elements are metal springs.

20. The device as claimed in claim 1, wherein the device has four drawing elements, of which two are respectively connected by means of a common lever.

21. The device as claimed in claim 20, wherein the drawing elements are bars.

22. The device as claimed in claim 20, wherein the drawing elements are metal springs.

23. The device as claimed in claim 1, wherein the drawing elements are bars.

24. The device as claimed in claim 1, wherein the drawing elements are metal springs.

* * * * *